United States Patent [19]

Bradley et al.

[11] Patent Number: 5,482,765
[45] Date of Patent: Jan. 9, 1996

[54] NONWOVEN FABRIC LAMINATE WITH ENHANCED BARRIER PROPERTIES

[75] Inventors: Stephen S. Bradley, Roswell; David C. Strack, Canton; Randall D. Lowery, Norcross; Deborah J. Zemlock; Mary K. Lawson, both Alpharetta, all of Ga.

[73] Assignee: Kimberly-Clark Corporation, Neenah, Wis.

[21] Appl. No.: 223,210

[22] Filed: Apr. 5, 1994

[51] Int. Cl.$^6$ .................................................. D04H 3/03
[52] U.S. Cl. .................... 428/286; 428/288; 428/289; 428/296; 428/303; 428/903; 428/297
[58] Field of Search .................................. 428/288, 284, 428/286, 297, 298, 289, 903

[56] References Cited

U.S. PATENT DOCUMENTS

| | | | |
|---|---|---|---|
| 3,125,547 | 3/1964 | Blatz | 260/45.5 |
| 3,338,992 | 8/1967 | Kinney | 264/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,859,330 | 1/1975 | Proskow | 260/47 UA |
| 3,907,604 | 9/1975 | Prentice | 136/146 |
| 3,909,009 | 9/1975 | Cvetko et al. | 274/37 |
| 4,013,816 | 3/1977 | Sabee et al. | 428/288 |
| 4,041,203 | 8/1977 | Brock et al. | 428/157 |
| 4,070,218 | 1/1978 | Weber | 156/167 |
| 4,196,245 | 4/1980 | Kitson et al. | 428/198 |
| 4,209,563 | 6/1980 | Sisson | 428/288 |
| 4,307,143 | 12/1981 | Meitner | 252/91 |
| 4,340,563 | 7/1982 | Appel et al. | 264/518 |
| 4,342,812 | 8/1982 | Selwood | 428/286 |
| 4,374,888 | 2/1983 | Bornslaeger | 428/198 |
| 4,443,513 | 4/1984 | Meitner et al. | 422/195 |
| 4,451,589 | 5/1984 | Morman et al. | 523/124 |
| 4,551,378 | 11/1985 | Carey, Jr. | 428/198 |
| 4,554,207 | 11/1985 | Lee | 428/288 |
| 4,555,811 | 12/1985 | Shimalla | 2/51 |
| 4,618,524 | 10/1986 | Groitzsch et al. | 428/198 |
| 4,622,259 | 11/1986 | McAmish et al. | 428/171 |
| 4,652,322 | 3/1987 | Lim | 156/181 |
| 4,677,017 | 6/1987 | DeAntonis et al. | 428/214 |
| 4,707,398 | 11/1987 | Boggs | 428/224 |
| 4,720,415 | 1/1988 | Wielen et al. | 428/152 |
| 4,863,785 | 9/1989 | Berman et al. | 428/218 |
| 4,863,983 | 9/1989 | Johnson et al. | 524/140 |
| 4,920,168 | 4/1990 | Nohr et al. | 524/188 |
| 4,960,820 | 10/1990 | Hwo | 524/528 |
| 4,965,122 | 10/1990 | Monman | 428/225 |
| 4,983,677 | 1/1991 | Johnson et al. | 525/127 |
| 5,021,501 | 6/1991 | Ohmori et al. | 524/544 |
| 5,165,979 | 11/1992 | Watkins et al. | 428/113 |
| 5,169,706 | 12/1992 | Colier, IV et al. | 428/152 |
| 5,173,356 | 12/1992 | Eaton et al. | 428/219 |
| 5,178,932 | 1/1993 | Perkins et al. | 428/198 |
| 5,188,885 | 2/1993 | Timmons et al. | 428/198 |
| 5,204,174 | 4/1993 | Daponte et al. | 428/286 |
| 5,213,881 | 5/1993 | Timmons et al. | 428/224 |
| 5,264,276 | 11/1993 | McGregor et al. | 428/252 |

FOREIGN PATENT DOCUMENTS

| | | |
|---|---|---|
| 0334829 | 9/1989 | European Pat. Off. |
| 0337662 | 10/1989 | European Pat. Off. |
| 0444671A3 | 9/1991 | European Pat. Off. |
| 0462574A1 | 12/1991 | European Pat. Off. |
| 1-246413 | 10/1989 | Japan. |
| 91/08254 | 6/1991 | WIPO. |
| 93/06168 | 4/1993 | WIPO. |

*Primary Examiner*—George F. Lesmes
*Assistant Examiner*—Kathleen L. Choi
*Attorney, Agent, or Firm*—James B. Robinson

[57] ABSTRACT

There is provided a laminate of nonwoven fabrics for barrier applications which has improved ratios of barrier and strength to weight, of softness to strength and of vapor transmission to barrier. The laminate has a meltblown layer sandwiched between spunbond layers to produce an SMS laminate. The meltblown and spunbond layers may have between 0.1 to 2.0 weight percent of a fluorocarbon and the meltblown layer preferably between 5 and 20 weight percent polybutylene. The laminate also may have pigments if desired. Such laminates are useful for garments.

14 Claims, No Drawings

NONWOVEN FABRIC LAMINATE WITH ENHANCED BARRIER PROPERTIES

BACKGROUND OF THE INVENTION

Noneoven fabrics are used for a wide variety of applications from baby wipes and diapers to automobile covers. These diverse applications call for materials having diverse properties and attributes. Some applications, for example, call for nonwovens which are highly wettable, i.e. quickly allow liquids to pass through them, e.g. liners for diapers and feminine hygiene products, while others require a high degree of repellency, e.g. outdoor fabrics and surgical fabrics. It is the latter class of products with which this invention is concerned, specifically, nonwoven materials which have superior barrier properties yet which have a high degree of vapor breathabilty.

Fabrics for surgical applications, for example as a surgical gown, must have good liquid barrier properties in order to protect medical personnel from contact with the bodily fluids of the patient yet must be breathable in order for the wearer's perspiration to pass through the fabric so as to remain comfortable. The fabric must also be strong enough to perform the desired function in the appropriate environment yet be soft and drapeable for the wearer's comfort and to avoid restricting the wearer's range of motion.

It is also important in many applications of nonwovens, for example as garments, for the finished product to be as lightweight as possible yet still perform its desired function. A lighter garment performing the same function as a heavier garment would be more comfortable for the wearer and probably less expensive to manufacture since less raw material would be necessary for its production.

A lighter weight, soft fabric having high liquid barrier properties, high vapor transmission and good strength would be of great utility in a diverse range of applications.

It is therefore an object of this invention to provide a soft nonwoven laminate having high liquid barrier properties, high vapor transmission and good strength.

SUMMARY

There is provided herein, in order to satisfy the objectives of the invention, a nonwoven laminate comprising a first layer of a nonwoven web formed of continuous filaments having an average diameter of greater than 10 microns and being prepared from a thermoplastic polymer which may be polyolefins, polyesters, polyamides, polyurethanes and copolymers and mixtures thereof, a second layer of a nonwoven web having a basis weight and formed of filaments having an average diameter of less than 10 microns and being prepared from a thermoplastic polymer which may be polyolefins, polyesters, polyamides, polyurethanes and copolymers and mixtures thereof, and a fluorocarbon compound in an amount from about 0.1 to 2.0 weight percent, a third layer of a nonwoven web formed of continuous filaments having an average diameter of greater than 10 microns and being prepared from a thermoplastic polymer which may be polyolefins, polyesters, polyamides, polyurethanes and copolymers and mixtures thereof, and where the layers are bonded to form a laminate having a ratio of hydrohead to second layer basis weight of greater than 115. The fabric should also have a ratio of WVTR to hydrohead of less than 75, a ratio of resistance to blood penetration to second layer basis weight of greater than 1, a ratio of cup crush to tensile strength of less than 150 and a ratio of BFE to meltblown basis weight of greater than 180. The first and/or third layers may also have a fluorocarbon in an amount from 0.1 to 2.0 weight percent. The second layer may be comprised of a mixture of polypropylene and between 5 and 20 weight percent polybutylene.

DETAILED DESCRIPTION OF THE INVENTION

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply by osy 33.91).

As used herein the term "microfibers" means small diameter fibers having an average diameter not greater than about 50 microns, for example, having an average diameter of from about 0.5 microns to about 50 microns, or more particularly, microfibers may desirably have an average diameter of from about 2 microns to about 40 microns.

As used herein the term "spunbonded fibers" refers to small diameter fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al. Spunbond fibers are generally continuous and larger than 7 microns, more particularly, having an average diameter of greater than 10 microns.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Meltblowing is well known in the art and is described, for example, in U.S. Pat. No. 3,849,241 to Buntin, U.S. Pat. No. 4,307,143 to Meitner et al., and U.S. Pat. No. 4,707,398 to Wisneski et al. Meltblown fibers are microfibers which are generally smaller than 10 microns in diameter.

As used herein the term "polymer" generally includes but is not limited to, homopolymers, copolymers, such as for example, block, graft, random and alternating copolymers, terpolymers, etc. and blends and modifications of any of the foregoing. Furthermore, unless otherwise specifically limited, the term "polymer" shall include all possible geometrical configuration of the material. These configurations include, but are not limited to isotactic, syndiotactic and random symmetries.

As used herein, the term "bonding window" means the range of temperature of the calender rolls used to bond the nonwoven fabric together, over which such bonding is successful. For polypropylene, this bonding window is typically from about 270° F. to about 310° F. (132° C. to 154° C.). Below about 270° F. the polypropylene is not hot enough to melt and bond and above about 310° F. the polypropylene will melt excessively and can stick to the calender rolls. Polyethylene has an even narrower bonding window.

As used herein, the terms "necking" or "neck stretching" interchangeably refer to a method of elongating a nonwoven fabric, generally in the machine direction, to reduce its width in a controlled manner to a desired amount. The controlled stretching may take place under cool, room temperature or greater temperatures and is limited to an increase in overall dimension in the direction being stretched up to the elongation required to break the fabric, which in many cases is about 1.2 to 1.4 times. When relaxed, the web retracts toward its original dimensions. Such a process is disclosed, for example, in U.S. Pat. No. 4,443,513 to Meitner and Notheis and another in U.S. Pat. No. 4,965,122 to Morman.

As used herein the term "neck softening" means neck stretching carried out without the addition of heat to the material as it is stretched, i.e., at ambient temperature.

In neck stretching or softening, a fabric is referred to, for example, as being stretched by 20%. This means to 80% of its original unstretched width.

As used herein, the term "neckable material" means any material which can be necked.

As used herein, the term "necked material" refers to any material which has been constricted in at least one dimension by processes such as, for example, drawing or gathering.

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have been elongated 50 percent and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the term "garment" means any type of apparel which may be worn. This includes industrial work wear and coveralls, undergarments, pants, shirts, jackets, gloves, socks, and the like.

As used herein, the term "medical product" means surgical gowns and drapes, face masks, head coverings, shoe coverings wound dressings, bandages, sterilization wraps, wipers and the like.

As used herein, the term "personal care product" means diapers, training pants, absorbent underpants, adult incontinence products, and feminine hygeine products and the like.

As used herein, the term "outdoor fabric" means a fabric which is primarily, though not exclusively, used outdoors. The applications for which this fabric may be used include car covers, boat covers, airplane covers, camper/trailer fabric, furniture covers, awnings, canopies, tents, agricultural fabrics and outdoor apparel.

TEST METHODS

Cup Crush: The softness of a nonwoven fabric may be measured according to the "cup crush" test. The cup crush test evaluates fabric stiffness by measuring the peak load required for a 4.5 cm diameter hemispherically shaped foot to crush a 23 cm by 23 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. The foot and the cup are aligned to avoid contact between the cup walls and the foot which could affect the peak load. The peak load is measured while the foot is descending at a rate of about 0.25 inches per second (38 cm per minute). A lower cup crush value indicates a softer laminate. A suitable device for measuring cup crush is a model FTD-G-500 load cell (500 gram range) available from the Schaevitz Company, Pennsauken, N.J. Cup crush is measured in grams.

Hydrohead: A measure of the liquid barrier properties of a fabric is the hydrohead test. The hydrohead test determines the height of water (in centimeters) which the fabric will support before a predetermined amount of liquid passes through. A fabric with a higher hydrohead reading indicates it has a greater barrier to liquid penetration than a fabric with a lower hydrohead. The hydrohead test is performed according to Federal Test Standard No. 191A, Method 5514.

Frazier Porosity: A measure of the breathability of a fabric is the Frazier Porosity which is performed according to Federal Test Standard No. 191A, Method 5450. Frazier Porosity measures the air flow rate through a fabric in cubic feet of air per square foot of fabric per minute or CSM. Convert CSM to liters per square meter per minute (LSM) by multiplying by 304.8.

Tensile: The tensile strength of a fabric may be measured according to the ASTM test D-1682-64. This test measures the strength in pounds and elongation in percent of a fabric.

Resistance to blood penetration: The resistance to blood penetration or RBP of a fabric is a measure of the maximum pressure at which no visible penetration of synthetic blood occurs through the nonwoven fabric for the duration of the test. This property is measured according to a modified ASTM test method ES21 in which the fabric is subjected to the test fluid at 0 psi for 5 minutes, the maximum pressure for 1 minute and then 0 psi for 54 minutes. The resistance to blood penetration is measured in pounds per square inch (psi).

WVTR: The WVTR of a fabric is water vapor transmission rate which gives an indication of how comfortable a fabric would be to wear. WVTR is measured in accordance with ASTM Standard Test Method for Water Vapor Transmission of Materials, Designation E-96-80.

Bacterial Filtration Efficiency: The Bacterial Filtration Efficiency (BFE) is a measure of the ability of a fabric to stop the passage of bacteria through it. A higher BFE is generally more desired, especially in medical applications. BFE is measured in percent according to military specification MIL-M-36954C, 4.4.1.1.1 and 4.4.1.2.

Melt Flow Rate: The melt flow rate (MFR) is a measure of the viscosity of a polymers. The MFR is expressed as the weight of material which flows from a capillary of known dimensions under a specified load or shear rate for a measured period of time and is measured in grams/10 minutes at 230° C. according to, for example, ASTM test 1238, condition E.

The field of nonwoven fabrics is a diverse one encompassing absorbent products such as diapers, wipes and feminine hygiene products and barrier products such as surgical gowns and drapes, and bandages. For applications in the latter field, a soft nonwoven laminate has been developed by the inventors which has good liquid repellency, good breathability and good strength. The particular components of personal care products where this fabric may be used are as leakage barriers such as containment flaps, outer covers and leg cuffs.

The fibers from which the fabric of this invention is made may be produced by the meltblowing or spunbonding processes which are well known in the art. These processes generally use an extruder to supply melted thermoplastic polymer to a spinnerette where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above.

The fabric of this invention is a multilayer laminate. An example of a multilayer laminate is an embodiment wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bornslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy.

Nonwoven fabrics are generally bonded in some manner as they are produced in order to give them sufficient structural integrity to withstand the rigors of further processing into a finished product. Bonding can be accomplished in a number of ways such as hydroentanglement, needling, ultrasonic bonding, adhesive bonding and thermal bonding.

Ultrasonic bonding is performed, for example, by passing the fabric between a sonic horn and anvil roll as illustrated in U.S. Pat. No. 4,374,888 to Bornslaeger.

Thermal bonding of a nonwoven fabric may be accomplished by passing the nonwoven fabric between the rolls of a calendering machine. At least one of the rollers of the calender is heated and at least one of the rollers, not necessarily the same one as the heated one, has a pattern which is imprinted upon the nonwoven fabric as it passes between the rollers. As the fabric passes between the rollers it is subjected to pressure as well as heat. The combination of heat and pressure applied in a particular pattern results in the creation of fused bond areas in the nonwoven fabric where the bonds on the fabric correspond to the pattern of bond points on the calender roll.

Various patterns for calender rolls have been developed. One example is the Hansen-Pennings pattern with between about 10 to 25% bond area with about 100 to 500 bonds/square inch as taught in U.S. Pat. No. 3,855,046 to Hansen and Pennings. Another common pattern is a diamond pattern with repeating and slightly offset diamonds.

The exact calender temperature and pressure for bonding the nonwoven web depend on thermoplastic(s) from which the web is made. Generally for polyolefins the preferred temperatures are between 150° and 350° F. (66° and 177° C.) and the pressure between 300 and 1000 pounds per lineal inch. More particularly, for polypropylene, the preferred temperatures are between 270° and 320° F. (132° and 160° C.) and the pressure between 400 and 800 pounds per lineal inch.

The thermoplastic polymers which may be used in the practice of this invention may be any known to those skilled in the art to be commonly used in meltblowing and spunbonding. Such polymers include polyolefins, polyesters, polyurethanes and polyamides, and mixtures thereof, more particularly polyolefins such as polyethylene, polypropylene, polybutene, ethylene copolymers, propylene copolymers and butene copolymers and mixtures thereof.

The spunbond layer of the fabric of this invention is preferably polyolefin, more particularly polypropylene having a melt flow rate (MFR) of between 9 and 1000, and still more particularly between 9 and 100. The MFR is an indication of the viscosity of the polymer with a higher number indicating a lower viscosity. Suitable polypropylenes for the spunbond layers are commercially available as PD-9355 from the Exxon Chemical Company of Baytown, Tex. The fibers of the spunbond layer should be of small diameter, preferably having a denier in the range of 1.5 to 2.2 or an average diameter of greater than 10 microns.

The meltblown layer of the fabric of this invention is also preferably polyolefin, particularly a combination of polypropylene and polybutylene, nonexclusive examples of which are those of U.S. Pat. Nos. 5,165,979 and 5,204,174. Still more particularly, a polypropylene having an MFR of between 200 and 5000 with from 0.5 to 20 weight percent of polybutylene. A suitable polypropylene has a melt flow rate of about 800 and is designated 3746-G from the Exxon Chemical Co., Baytown, Tex., and a suitable polybutylene is available as DP-8911 from the Shell Chemical Company of Houston, Tex.

The meltblown web of this invention also may contain a polypropylene modified according to U.S. Pat. No. 5,213,881. This patent claims a nonwoven web of fine fibers formed from polymer streams where the fibers have an average size of from 1 to 3 microns, the web has pore sizes distributed predominantly in the range of from 7 to 12 microns with the peak of the pore size distribution of less than 10 microns, the polymer streams are made from reactor granules of a modified propylene polymer polymerized with a Ziegler-Natta catalyst and where the polymer has a molecular weight distribution between 2.8 and 3.5 Mw/Mn and a modified polymer melt flow rate greater than 3000 grams/10 min. at 230° C. The modified propylene polymer may be the result of adding up to 3000 ppm of peroxide to the reactor granules prior to forming the web.

The meltblown layer of the fabric of this invention contains a fluorocarbon chemical to impart low surface tension liquid repellency which may be any of those taught in U.S. Pat. No. 5,178,931, column 7, line 40 to column 8, line 60. A particularly well suited additive is FX-1801, formerly called L-10307, which is available from the 3M Company of St. Paul, Minn. This material is identified as Additive M in the above cited patent and as having a melting point of about 130° to 138° C. This material is added to the meltblown layers at an amount of about 0.1 to about 2.0 weight percent or more particularly between about 0.25 and 1.0 weight percent. As noted in the above patent, the fluorocarbon additive is an internal additive, as differentiated from a topically applied additive, and preferentially migrates to the surface of the meltblown fibers as they are formed.

The spunbond layer of the fabric of this invention may also have a fluorocarbon additive. This may be the same additive as the meltblown layer and may be present in an amount between 0.1 and 2.0 weight percent.

The layers of the fabric of this invention may also contain fire retardants for increased resistance to fire, pigments to give each layer the same or distinct colors, and/or chemicals such as hindered amines to provide enhanced ultraviolet light resistance. Fire retardants and pigments for spunbond and meltblown thermoplastic polymers are known in the art and are internal additives. A pigment, if used, is generally present in an amount less than 5 weight percent of the layer.

The fabric of this invention may also have topical treatments applied to it for more specialized functions. Such topical treatments and their methods of application are known in the art and include, for example, anti-static treatments and the like, applied by spraying, dipping, etc. An example of such a topical treatment is the application of Zelec® antistat (available from E.I. dupont, Wilmington, Del.).

The fabric of this invention may also be neck stretched as taught in the above cited patents. Neck stretching or softening serve to soften the fabric yet do not remove an unacceptable degree of sheet properties.

Since a lighter weight fabric having the same properties as a heavier fabric is generally the most desired, the properties of the fabric of this invention were compared on the basis of weight as well as on the basis of barrier.

The above mentioned characteristics of the fabric of this invention are illustrated by the examples below, results of the testing of which are given in Table 1. Note that Examples 1 & 2 are examples of the fabric of this invention and the other is not.

EXAMPLE 1

A laminate was produced comprising a meltblown layer of about 0.5 osy (17 gsm) between two layers of spunbond material of about 0.55 osy (18.7 gsm) for a final SMS laminate with about a 1.6 osy (54 gsm) basis weight. The spunbond layers were made from polypropylene copolymer designated PD-9355 by Exxon Chemical Co. The meltblown layers were made from polypropylene designated 3746G from Exxon Chemical. The meltblown layers contained FX-1801 fluorocarbon in an amount of about 1 weight percent and Shell DP-8911 polybutylene in an amount of about 10 weight percent. This fabric was neck softened by 8 percent at ambient temperature.

EXAMPLE 2

A laminate was produced comprising a meltblown layer of about 0.5 osy (17 gsm) between two layers of spunbond material of about 0.5 osy (17 gsm) for a final SMS laminate slightly lighter than Example 1 at about a 1.5 osy (51 gsm) basis weight. The spunbond layers were made from polypropylene copolymer designated PD-9355 by Exxon Chemical Co. and one of the spunbond layers contained the 3M Corporation's FX-1801 fluorocarbon in an amount of about 0.25 weight percent. The meltblown layers were made from polypropylene designated 3746G from Exxon Chemical. The meltblown layers contained FX-1801 fluorocarbon in an amount of about 0.75 weight percent and Shell DP-8911 polybutylene in an amount of about 10 weight percent. This fabric was neck softened by 8 percent at ambient temperature.

TABLE 1

|  | Evol. 3* | Ex. 1 | Ex. 2 |
| --- | --- | --- | --- |
| Laminate basis weight (osy) | 1.6 | 1.6 | 1.5 |
| Meltblown basis weight (osy) | 0.5 | 0.5 | 0.5 |

TABLE 1-continued

|  | Evol. 3* | Ex. 1 | Ex. 2 |
| --- | --- | --- | --- |
| Hydrohead (cm) | 53 | 92 | 96 |
| RBP (psi) | 0.2 | 0.7 | 0.8 |
| WVTR (g/m$_2$/day) | 4520 | 4830 | 4720 |
| Cup Crush (gm) | 4355 | 3640 | 2375 |
| CD Tensile strength (lb) | 18.3 | 13.6 | 16.5 |
| MD Tensile strength (lb) | 20.5 | 18.0 | 22.3 |
| CD Elongation | 57 | 69 | 80 |
| MD Elongation | 43 | 57 | 60 |
| BFE (%) | 87 | 96 | 96 |

Evol. 3* This material is commercially available from the Kimberly-Clark Corporation of Neenah, Wisconsin, as part of a surgical gown under the trade designation Evolution ® 3. It is a three layer, SMS laminate with two polypropylene spunbond layers and a polypropylene meltblown layer.

The key ratios for determining the various properties based on the meltblown layer weight and barrier qualities are given Table 2 below for the two fabrics of Table 1 using the units given in Table 1. The most important ratio is the barrier (hydrohead) to the weight of the meltblown layer since it will indicate if a lighter weight fabric may be produced with comparable barrier properties to those already available. The meltblown layer is the layer primarily responsible for the barrier properties.

TABLE 2

|  | Evol. 3 | Ex. 1 | Ex. 2 |
| --- | --- | --- | --- |
| Hydrohead to meltblown basis wt. | 106 | 184 | 190 |
| RBP to MB basis wt. | 0.4 | 1.4 | 1.6 |
| BFE to MB basis weight | 174 | 192 | 192 |
| WVTR to Hydrohead | 85 | 53 | 49 |
| Cup crush to CD tensile strength | 240 | 270 | 145 |
| Cup crush to MD tensile strength | 212 | 202 | 107 |
| Cup crush to CD elongation | 57 | 69 | 80 |
| Cup crush to MD elongation | 43 | 57 | 60 |

It has been found that the fabric made in accordance with this invention usually has ratios in the ranges found in Table 3, using the units of Table 1.

TABLE 3

|  | This invention |
| --- | --- |
| Hydrohead to meltblown basis weight | >115 |
| RBP to meltblown basis wt. | >1.0 |
| BFE to meltblown basis wt. | >180 |
| WVTR to Hydrohead | <75 |
| Cup crush to tensile strength | <150 |

Thus it has been shown that a fabric made in accordance with this invention is strong, has better barrier properties and breathability, and is softer than other fabrics at about the same basis weight. Keeping the barrier properties of this novel fabric about equivalent with current laminates would allow the production of a thinner, lighter weight material with accompanying reduction in raw material, production, and disposal costs, etc. and an increase in comfort for the wearer.

I claim:

1. A nonwoven laminate comprising:
   a first layer of a nonwoven web having a basis weight between 5 and 70 gsm and comprising continuous filaments having an average diameter of greater than 10 microns and being prepared from a thermoplastic polymer;
   a second layer of a nonwoven web having a basis weight between 5 and 70 gsm and comprising filaments having an average diameter of less than 10 microns and being prepared from a mixture of a thermoplastic polyolefin, from about 5 to about 15 weight percent polybutylene, and a fluorocarbon compound in an amount from about 0.1 to 2.0 weight percent to impart low surface tension liquid repellency;

a third layer of a nonwoven web having a basis weight between 5 and 70 gsm and comprising continuous filaments having an average diameter of greater than 10 microns and being prepared from a thermoplastic polymer;

wherein said layers are thermally bonded to form a laminate having a ratio of hydrohead to said second layer basis weight of greater than 115 cm/osy, a ratio of resistance to blood penetration to said second layer basis weight of greater than 1 psi/osy, and a ratio of WVTR to hydrohead of less than 75 g/m$^2$/day per cm.

2. The nonwoven laminate of claim 1 wherein said first and/or third layer further comprises a fluorocarbon compound in an amount from about 0.1 to 2.0 weight percent.

3. The nonwoven laminate of claim 1 wherein said first and/or third layer further comprises a topically applied antistatic treatment.

4. The nonwoven laminate of claim 1 which has been necksoftened.

5. The laminate of claim 1 wherein said thermoplastic polymer in said second layer is a polypropylene which has a melt flow rate of around 3000 grams/10 minutes.

6. The laminate of claim 1 wherein at least one of said layers has pigment present in an amount less than 5 weight percent.

7. The laminate of claim 1 in the form of a surgical gown.

8. The laminate of claim 1 in the form of a face mask.

9. The laminate of claim 1 in the form of a sterilization wrap.

10. The laminate of claim 1 in the form of a car cover.

11. The laminate of claim 1 in the form of a boat cover.

12. The laminate of claim 1 in the form of a camper/trailer fabric.

13. The laminate of claim 1 in the form of an agricultural fabric.

14. The laminate of claim 1 wherein said laminate has a ratio of BFE to second layer basis weight of greater than 180 percent/osy.

* * * * *